United States Patent [19]
Allbritton et al.

[11] Patent Number: 6,156,576
[45] Date of Patent: Dec. 5, 2000

[54] FAST CONTROLLABLE LASER LYSIS OF CELLS FOR ANALYSIS

[75] Inventors: Nancy L. Allbritton; Christopher E. Sims, both of Irvine; Michael W. Berns, Coto de Caza; Gavin D. Meredith, Cardiff-By-The-Sea; Tatiana B. Krasieva; Bruce J. Tromberg, both of Irvine, all of Calif.

[73] Assignee: The Regents of the University of California, Oakland, Calif.

[21] Appl. No.: 09/036,706

[22] Filed: Mar. 6, 1998

[51] Int. Cl.[7] .................................................. G01N 33/48
[52] U.S. Cl. .......................... 436/63; 436/164; 436/172; 422/82.05; 422/82.08; 435/4; 435/29; 435/288.7; 204/451; 204/452; 204/453; 204/403; 204/601; 204/603; 204/604
[58] Field of Search ............................ 436/63, 164, 172; 422/82.05, 82.08; 435/4, 29, 30, 288.7; 204/450–453, 600, 601, 603, 604, 194, 400, 403

[56] References Cited

U.S. PATENT DOCUMENTS

| | | | |
|---|---|---|---|
| 4,469,098 | 9/1984 | Davi | 606/7 |
| 5,071,417 | 12/1991 | Sinofsky | 606/8 |
| 5,212,382 | 5/1993 | Sasaki et al. | 250/251 |
| 5,359,615 | 10/1994 | Sasaki et al. | 372/39 |
| 5,393,957 | 2/1995 | Misawa et al. | 219/121.85 |
| 5,458,761 | 10/1995 | Kamahori et al. | 204/602 |
| 5,498,324 | 3/1996 | Yeung et al. | 204/452 |
| 5,505,831 | 4/1996 | Liao et al. | 204/451 |
| 5,565,171 | 10/1996 | Dovichi et al. | 422/68.1 |
| 5,567,292 | 10/1996 | Madabhushi et al. | 204/451 |
| 5,618,285 | 4/1997 | Zair | 606/10 |
| 5,627,643 | 5/1997 | Birnbaum et al. | 356/344 |
| 5,679,536 | 10/1997 | Hayashi et al. | 435/7.9 |

OTHER PUBLICATIONS

Sims et al. *Analytical Chemistry*, vol. 70, No. 21, pp. 4570–4577, Nov. 1, 1998.
Abstract—Kirkpatrick et al. *Energy Res. Abstracts* vol. 4, No. 15, Abstr. No. 41711, 1979.
Abstract—Theis et al. *Clinical Cardiology*, vol. 6, No. 8, pp. 396–398, 1983.
Abstract—Solgonick et al. *Journal of Endourology* vol. 7, No. 5, pp. 371–373, Oct. 1993.
Abstract—Krasieva et al. *Proc. SPIE—Int. Soc. Opt. Eng.*, vol. 3260, pp. 38–44, 1998.
Trends in Capillary Electrophoresis: 1977, Journal of Chromatographic Science, vol. 35, Aug. 1997, Qing Yang et al, pp. 358–372.

(List continued on next page.)

*Primary Examiner*—Maureen M. Wallenhorst
*Attorney, Agent, or Firm*—Daniel L. Dawes

[57] ABSTRACT

Fast lysis of a single cell or cellular component thereof is performed by generating a shock wave in a medium in which the cell or cellular component thereof is positioned. The cell or cellular component thereof is either positioned by laser tweezers or cultured as an adhered cell or cellular component thereof to minimize manipulation trauma. The disclosed method completely lyses a single cell or cellular component thereof in a controllable manner in milliseconds or less followed immediately by the loading of the cellular contents into a capillary for analyte separation and detection. The cell or cellular component thereof is adjacent the inlet of an electrophoretic column through which a gravity siphon flow of the medium is maintained. The lysed contents of the cell or cellular component thereof enter the electrophoretic column in less than 33 msec, are separated and analyzed by laser induced fluorescence. The method takes advantage of the shock wave produced by a highly focused laser pulse which is created in a medium adjacent to the cell or cellular component thereof. In the illustrated embodiment the laser pulse is focused in the glass substrate at or near a glass-to-buffer interface of a cell chamber in which the cell or cellular component thereof to be lysed has been cultured.

45 Claims, 7 Drawing Sheets

OTHER PUBLICATIONS

Chemical Analysis of Single Cells and Exocytosis, Critical Reviews in Neurobiology, 11, Guangyao Chen et al., pp. 59–90, 1997.

Assaying single cells with capillary electrophoresis, Trends in Analytical chemistry, vol. 14, No. 4, 1995, Jeffrey A. Jankowski et al., pp. 170–176.

Capillary Zone Electrophoresis with Electrochemical Detection in 12.7 um Diameter Columns, Anal. Chem. 1988, 60, Wallingford, et al., pp. 1972–1975.

Capillary Electrophoresis in 2 and 5 um Diameter Capillaries: Application to Cytoplasmic Analysis, Anal. Chem, 1990, 62, Olefirowicz et al. pp. 1872–1876.

Microcolumn Separations and the Analysis of Single Cells, Articles, Kennedy et al., pp. 57–63, Oct. 6, 1989.

Nitrite and Nitrate Levels in Individual Molluscan Neurons: Single–Cell Capillary Electrophoresis Analysis, Journal of Neurochemistry, Cruz, pps 110–115, 1997.

Determination of Intracellular Species at the Level of a Single Erthyrocyte, etc. American Chemical Society 1992, Hogan et al., pp. 2841–2845.

Monitoring Exocytosis and Releasing from Individual Mast Cells, etc. Analytical Chemistry, vol. 68, No. 17, 1996, Lillard et al., pp. 2897–2904.

Monitoring single–cell pharmacokinetics by capillary electrophoresis, etc. Journal of Chromatography B, 689, 1997, Tong et al., pp. 321–325.

Discovery of endogenous catecholamines in lymphocytes and evidence for, etc. Proc. Natl. Acad. Sci, USA, Bergquist et al., pp. 12912–12916, Dec. 1994.

Analysis of Single Cells by Capillary Electrophoresis with On–Column, etc. Analytical Chemistry vol. 67, No. 1, 1995, Gilman et al., pp. 58–64.

Kinetic Perfection in Enzymatic Catalysis:et al., Biochemistry textbook by Stryer, pp. 1995, Date Unknown.

Inositol Trisphosphate and calcium signalling, Nature, vol. 361, 1993 Berridge, pp. 315–325.

A review of In Vitro Studies: Low–Frequency Electromagnetic Fields, American Industrial Hygiene Assoc., Cleary, 1993, pps 178–185.

A critical review of the genotoxic potential of electric and magnetic fields, Mutation Research, 1993, McCann et al., pp. 61–95.

Formation and resealing of pores of controlled sizes in human erythrocyte membrane, Nature vol. 268, 1997, Kinosita, JR et al., pp. 438–441.

Electroporation–Induced Formation of Individual Calcium Entry Sites et al. Biophysical Journal vol. 73, 1997, Teruel et al., pp. 1785–1796.

Microcolumn separations of single nerve call components, Journal of Neuroscience Methods, 1993, Ewing, pp. 215–224.

Manipulation of a single cell with microcapillary tubing based on its electrophoretic mobility, Electrophoresis 1995, Kitagawa et al., pp. 1364–1368.

Focal Adhesions, Contractility, and Signaling, Annual Reviews Inc. 1996, Burridge et al., pp. 463–519.

Regulation of extracellular matrix synthesis by mechanical stress, Biochem. Cell Biol. 74, 1996, Chiquet et al., pp. 737–744.

Tensegrity: The Architectural Basis of Cellular Mechanotransduction, Annual Reviews Inc. 1997, Ingber, pp. 575–599.

Mechanisms of Intraocular Photodisruption with Picosecond and Nanosecond Laser Pulses, Lasers in Surgery and Medicine 1994, Vogel et al., pp. 32–43.

The Interaction of a single laser–generated cavity in water with a solid surface, 1996 Acoustical Society of America, Shaw et al., pp. 2811–2823.

Shock wave emission and cavitation bubble generation by picosecond and nanosecond optical breakdown in water, 1996 Acoustical Society of Am. Vogel, pp. 148–165.

Alteration of cell membrane by stress waves In Vitro, Ultrasound in Med. & Biol., vol. 22, No. 9, 1996, Lee et al., pp. 1285–1293.

Stress–Wave–Induced Injury to Retinal Pigment Epithelium Cells In Vitro, Lasers in Surgery and Medicine 1996, Douki et al., pp. 249–259.

Transcellular transport of fluorescein in hepatocyte monolayers: et al, Proc. Natl. Acad. Sci. USA, vol. 79, Aug. 1982, Barth et al., pp. 4985–4987.

Volumetric Constraints on Injection Size, Practical Capillary Electrophoresis by Weinberger, Jr., pp. 197–200, Date Unknown.

Localized Sampling of Cytoplasm from Xenopus Oocytes for Capillary Electrophoresis Analytical Chemistry, vol. 69, No. 23, Luzzi et al, pp. 4761–4767, 1997.

Direct gene transfer into human cultured cells facilitated by laser micropuncture of the cell membrane, Proc. Natl. Acad. Sci. USA, vol. 84 1987, Tao et al pp. 4180–84.

Injection of Ultrasmall Samples and Single Molecules into Tapered Capillaries, Anal. Chem. 1997, Chiu et al., pp. 1801–1807.

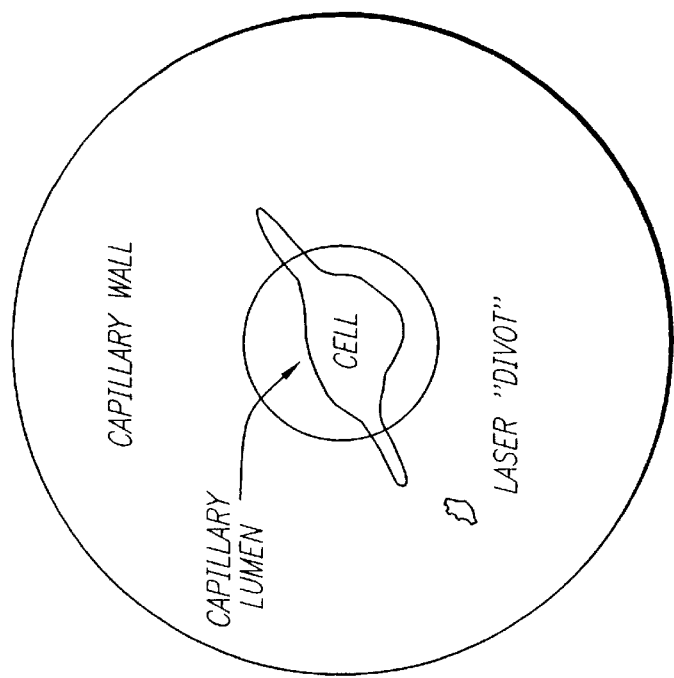
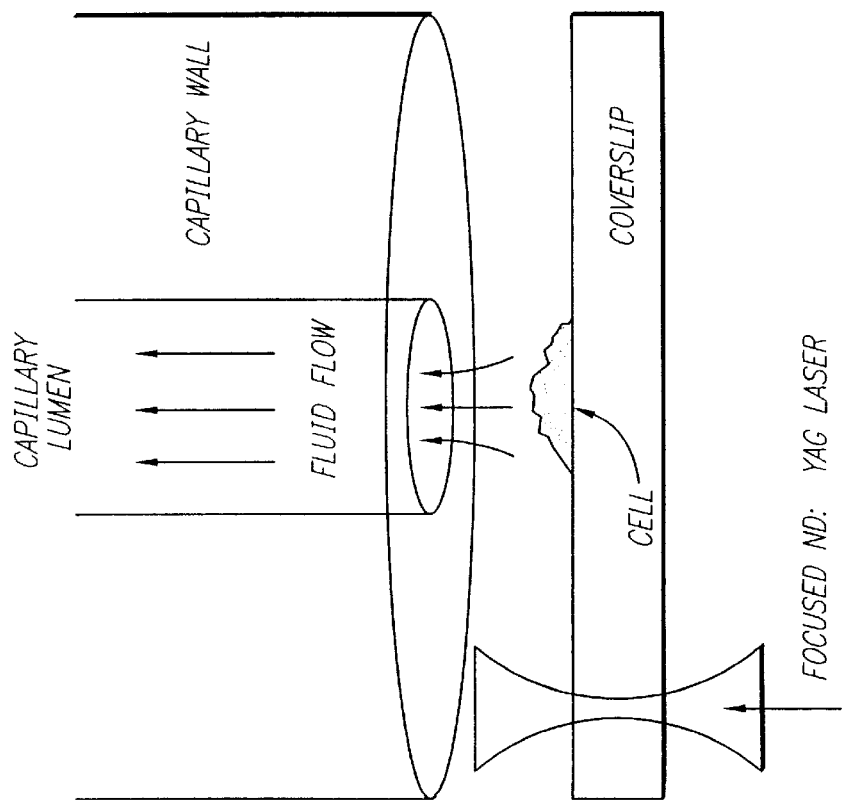

PRE-LYSIS

LYSIS

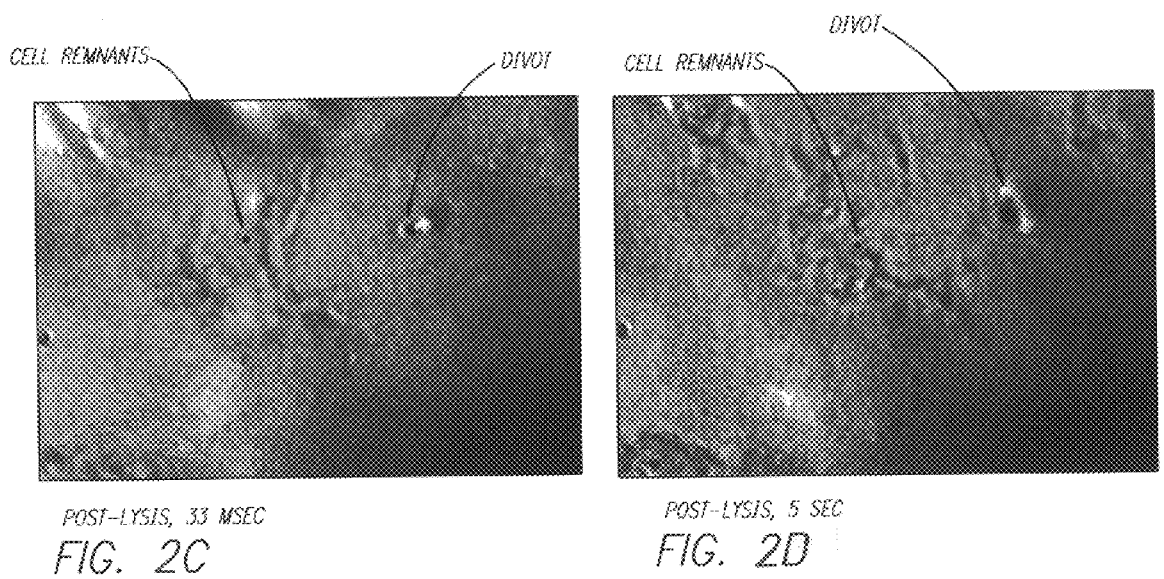

PRE-LYSIS

— CAPILLARY LUMEN
— RBL CELL

LYSIS

— CIRCULAR WAVE

— REFLECTION

POST-LYSIS, 33 msec

— DIVOT

FAST CONTROLLABLE LASER LYSIS OF CELLS FOR ANALYSIS

BACKGROUND OF INVENTION

1. Field of the Invention

The invention relates to the field of analytical chemistry in the areas of cellular biochemical and biomedical analysis and in particular to a laser microsurgery apparatus and method performed in less than one second for controllably lysing a single cell or selected cells and then collecting all or a selected portion of the cellular contents for immediate chemical analysis.

2. Description of the Prior Art

Dramatic progress in our understanding of biological processes has been made possible by studies of single cells. Research directed at the individual cells of an organism has utilized recent technological advances in optical and chemical methods. Laser-based techniques for manipulation of single cells and subcellular structures have enabled the performance of surgery on single cells. Ultrasensitive chemical analysis methods have now been used in biochemical studies of single cells. New knowledge gained from such single-cell studies is already finding medical and commercial applications. It can be expected that technology for the manipulation and analysis of single cells will play an important role in such areas as biomedical research, drug discovery, diagnosis of disease, and medical treatment.

In the past decade the tools of the analytic chemist have been applied to biochemical studies of living cells. For example, single neuronal cells from nonmammalian species have been analyzed through the use of capillary electrophoresis. By virtue of the large size of these neuronal ganglion cells subcellular measurements have been possible. Typically these cells are approximately 0.1 to 0.2 millimeters in diameter. In the prior art technique, the end lead of a capillary is etched to a fine point and used to sample cytoplasm from a cell or disrupted cellular fragment. Cytoplasmic contents are separated within the capillary and either detected on or off line.

For smaller mammalian cells in the range of 10 to 15 microns in diameter, the entire cell is loaded into the capillary and then the cell is lysed with a hypotonic or detergent-containing buffer. The cellular contents are separated in the capillary and detected by a variety of methods such as laser induced fluorescence or eletrochemical detection. However, cellular lysis is not easily controllable either as to the time at which it takes place or over the duration during which it occurs. For measurements on mammalian cells, the temporal resolution of the measurement techniques and the effects of perturbing the cell prior to complete lysis are important issues to consider. Lysis is defined for the purposes of this specification as the disruption of at least a portion of the plasma membrane with the release of at least a portion of the cellular contents. The manner in which the cell is lysed will govern the time which is required to terminate the biochemical reactions in progress, that is the manner of lysis will govern the temporal resolution of the biological measurement. Also, the manner of lysis will influence cellular processes occurring during the period of sampling. Many biological events take place on time scales of seconds or less. The enzymes typically have turnover numbers on the order of one to ten thousand per second. Metabolite concentrations can change greater than ten-fold in one second. Accurate measurement of such cellular properties by analytical techniques requires then that complete cell lysis occurs rapidly in comparison to the rate of change of the measured parameter. If disruption of the cell membrane occurs at a rate which is too slow, significant changes in the parameter can occur during the very lysis of the cell resulting in an inaccurate view of the actual physiological state of the cell.

In addition, membrane permeabilization during lysis results in the influx of extracellular ions such as calcium ($Ca^{2+}$), activating many enzymes including kinases, phosphatases, proteases and nucleases. Even after disruption of the plasma membrane, biochemical processes will proceed until reactions are terminated, that is by separation of the reactants or denaturation of the molecules. Therefore, in order to accurately measure many cellular processes, complete cell lysis must be performed within milliseconds or less. The prior art chemical lysis is incapable of providing this speed in any manner which is controllable so that effective cellular analysis is possible.

Another important consideration in making whole cell measurements is the effect caused by manipulation of the cell prior to sampling. In studies of nonadherent or free floating cells using capillary electrophoresis the use of electroosmotic flow to move the cell into the capillary inlet may impact the cell and hence the process which is to be measured. A large body of literature exists on the biological effects of electrical fields. Unfortunately, most of the literature addresses AC rather than static fields so that the effects of low DC electric field strengths on cellular physiology have not been well characterized. However, there is no doubt that there is some effect. Application of an electric field with a gradient of the order of 1–2 kV/cm, can induce permeabilization of the cell membranes, a phenomenon known as electroporation. The potential gradients below 1–2 kV/cm, which are generally used for capillary electrophoresis, namely on the order of 400 V/cm, have important effects on cellular physiology. At an electric field strength of 167 V/cm for a five millisecond duration, there were localized increases in cellular permeability with concomitant influx of calcium ions ($Ca^{2+}$) has been demonstrated. Such calcium ion influx can activate numerous cellular processes that may affect biochemical measurements.

In order to move a cell into a capillary, investigators have induced electroosmotic flow using potential gradients varying from 10 V/cm to 300 V/cm. While potential gradients in the range of 10–20 V/cm are unlikely to perturb cellular physiology, higher field strengths most certainly will.

Adherent cells or cells that adhere to a substrate, such as a glass slide or pipette are not amenable to manipulation by electroosmotic flow or hydrodynamic flow without first removing them from their attaching substrate. However, the mechanical stress induced by such removal can trigger a variety of cellular responses. Nearly all cells express abundant adhesion proteins at their surfaces. Structures known as focal adhesions provide a structural link between the cytoskeleton and the extracellular matrix. Focal adhesions consist of integrins and other proteins which are linked to a variety of intracellular signal transduction pathways. Mechanical stresses act through these membrane components to activate numerous enzymes including tyrosine kinases, serine/threonine kinases, G-proteins, proteases and others. Activations of these pathways trigger immediate and long term changes in the cellular physiology. For this reason mechanical manipulation, especially with adherent cells, prior to the time of sampling may interfere with measurement of the cellular biochemistry.

What is needed is a method to completely or at least partially lyse a single cell in milliseconds or less in a manner which is controlled both as to time and place and which does not affect the cellular physiology prior to lysis followed by loading of the cellular contents into a device for analysis such as a capillary for analyte separation and detection.

BRIEF SUMMARY OF INVENTION

The invention is a method for lysing and analysis of the contents of a selected cell or cellular component thereof comprising the steps of controllably selecting at least one of a plurality of cells or cellular component thereof in a medium. The selected cell or cellular component is disrupted or lysed with a laser generated shock wave in the medium or in a substrate or glass surface some distance from the cell. At least a portion of the contents of the cell or cellular component is collected. The collected contents are then analyzed.

In the illustrated embodiment the contents of the cell or cellular component thereof is collected within one second or less of lysis of the cell. This is of utility when the cell is living so that the biological reactants can be analyzed in the state which they had obtained at the instant of lysis. In fact the contents are collected within 33 msec or less of lysis of the cell and it is believed that collection is delayed only by the time for the cell or cellular component to porate or open, which is believed to be a few microseconds or in the range of 1–10 microseconds of lysis of the cell. As a result, the time between disruption of cellular biochemical activity and the cessation of reactions of the cellular contents is minimized, yielding a very accurate view of the cellular contents immediately prior to lysis. However, the invention is applicable to other applications as well, such as the lysis or rupture of dead cells, where the time between lysis and cessation of reactions is not as critical.

The step of controllably selecting at least one of a plurality of cells or cellular components comprises the steps of identifying and determining the position of the selected cell or cellular component thereof. Either the identified cell or component can be brought to the position near the focal point of the laser beam and collection inlet, or the position of focal point of the laser beam and collection inlet can be brought near the identified cell or component.

One method to controllably position the selected cell or cellular component in the medium comprises the step of adhering the cell or cellular component thereof to a substrate disposed at least adjacent to the medium.

Where the cell or cellular component is free floating the step of controllably positioning the selected cell or cellular component in the medium in another embodiment comprises the step of temporarily holding the cell or cellular component in a position in the medium by a laser microbeam optical tweezers, or temporarily holding the cell or cellular component in a position in the medium by adhesion of a mechanical micromanipulator to the cell or cellular component. The cell or cellular component can be attached to a pipette or microprobe either by suction or by means of electrical or chemical adhesion.

The process may be practiced under human control or by automated software control. For example, the field of view within a target zone adjacent to the inlet of the analysis device is optically monitored by a video system coupled to a computer provided with pattern recognition software or by a human operator. When a target cell is properly positioned in the target zone and identified as a desired target, a laser pulse is generated that produces a shock wave which lyses the cell followed by immediate collection into the analysis device.

Still further the free floating cell or cellular component can be controllably positioned in the medium by positioning the cell or cellular component in a confined enclosure such as the inlet to the analysis device or a holding enclosure in which the cell is positioned.

The step of collecting at least a portion of the contents of the cell or cellular component thereof may further comprise the step of stopping the reactions of biochemical reactants disrupted from the selected cell or cellular component thereof to permit subsequent analysis of the biochemical reactants in the state which existed approximately at the time of disruption.

In the illustrated embodiment the step of collecting the contents of the disrupted cell or cellular component in the analysis device comprises the step of collecting the cell or cellular component in an electrophoretic column. The collected contents are electrophoretically separated and analyzed using laser induced fluorescence.

The step of disrupting the selected cell or cellular component with a laser generated shock wave in the medium comprises in one embodiment the step of focusing a pulsed laser beam at a position proximate to the cell or cellular component, but without focusing on the cell or cellular component and then generating the shock wave.

In another embodiment the pulsed laser beam is focused directly in or on the cell or cellular component. The pulsed laser beam defines an opening in the cell or cellular component to obtain only cytoplamsic contents therefrom.

In the illustrated embodiment the step of collecting at least a portion of the contents of the disrupted cell or cellular component thereof in the analysis device is by means of fluid flow of the medium, and in particular by means of siphon fluid flow of the medium. Collection can also be effected by means of electrophoresis through the medium, by means of force from the shock wave impacted on the contents, and by means of electroosmotic force.

The invention is alternatively defined as an apparatus for lysing and analysis of the contents of one of a plurality of cells or cellular components thereof comprising a cell selector to controllably select at least one of the cells or cellular component thereof. A laser generates a pulse to lyse or rupture the selected cell or cellular component. An analysis device is provided to analyze the contents. A collector captures or delivers at least a portion of the contents of the lysed cell or cellular component to the analysis device.

The collection after lysis and the lysis itself is fast. The collector delivers at least a portion of the contents of the lysed cell or cellular component to the analysis device within one second of lysis of the cell or cellular component. Where applied to a living cell the contents of the lysed cell or cellular component is delivered to the analysis device within 33 msec of lysis of the cell or cellular component and in all probability within 1–10 microseconds of lysis of the cell or cellular component.

The analysis device may be any microanalytical chemical, electrical or electrochemical device or technology such as a means for performing polymerase chain reactions on the contents, a means of separating analyte molecules such as a gel or capillary electrophoretic column, and a means for detecting separated analytes such as a gel reader or a laser induced fluorescence detector.

The invention is also defined as a method for fast lysing and analysis of the contents of one of a plurality of cells or cellular components thereof comprising the steps of controllably selecting at least one of the plurality of cells or cellular components thereof by relative placement of the selected cell or component adjacent to an inlet orifice of a pipette. The selected cell or cellular component thereof is lysed with a laser generated pulse. At least a portion of the contents of the lysed cell or cellular component thereof is collected in the pipette within one second of lysis for subsequent analysis. Any further substantial biologic reactions in the contents are stopped after lysis.

The invention and its various embodiments, now having been summarized, may be better understood by viewing the following drawings wherein like elements are referenced by like numerals.

BRIEF DESCRIPTION OF THE DRAWING

FIG. 1B is a magnified diagrammatic side view of the area in the vicinity of the inlet of the capillary used in FIG. 1A showing the position of the capillary inlet with respect to a single cell and with respect to a location of a focused laser pulse.

FIG. 1C is a magnified diagrammatic bottom view of the area in the vicinity of the inlet of the capillary used in FIGS. 1A and B showing the position of the capillary inlet with respect to a single cell and with respect to a location of a focused laser pulse.

FIGS. 2A–D are video still images taken before and after lysis. FIG. 2A is a microphotograph of a cell taken immediately prior to lysis of the cell.

FIG. 2B is a video frame at the instant of the start of lysis when applied according to the invention. The focal point of the laser is just below the surface of the cover slip so the cell is slightly out of focus. The bright image shown by the arrow is the reflected image and not the actual laser pulse.

FIG. 2C is a video frame of the cell 33 msec after lysis. Cell remnants and secretory granules can be seen. The divot in the glass caused by the interaction of the laser with the glass substrate is also visible.

FIG. 2D is the same video frame as shown in FIG. 2C but with the focal plane adjusted to match that as shown in FIG. 2A in order to better resolve the cell remnants in the image.

FIG. 3A shows the cell immediately prior to the laser pulse being applied.

FIG. 3B shows a circular wave emanating from the point of a laser pulse which has not yet interacted with the cell.

FIG. 3C shows the cell subsequent to lysis. The cell remnants and contents have been loaded into the capillary and are no longer visible in the image. The laser induced defect in the cover slip is visible.

The invention and its various embodiments may now be understood by turning to the following Detailed Description of the Preferred Embodiments.

DETAILED DESCRIPTION OF THE PREFERRED EMBODIMENTS

The illustrated method completely lyses a single cell in a controllable manner in milliseconds or less followed immediately by the loading of the cellular contents into a capillary for analyte separation and detection. The method takes advantage of the shock wave produced by a highly focused laser pulse which is created in a medium adjacent to the cell. The laser could also be focused (a) in the glass slide adjacent to the cell, (b) in a substrate disposed on the glass slide, (c) in the fluid at the interface of the glass slide or substrate, or (d) in the fluid adjacent to the target cell in the case where the cell is free floating or being held by optical tweezers. In the illustrated embodiment the laser pulse is focused in the glass substrate at or near a glass-to-buffer interface of a cell chamber in which the cell to be lysed has been cultured or attached. It must be understood that the laser pulse may be focused at other locations such as on the cell wall or membrane itself, where for example a cytoplasmic puncture is desired to remove just a portion of the cell contents, or may be focused at any position in the fluid surrounding the cell in the cell chamber. In the illustrated embodiment a 5 nsec laser pulse is used to cause a localized plasma. The formation of the plasma at the focal point is believed to produce a cavitation bubble in the fluid medium nearby. The expansion and collapse of this cavitation bubble generates a supersonic or near supersonic shock wave traveling up to 2,000 m/sec. For a cell 20 microns in diameter such a shock completely traverses the cell in 10 nsec. Therefore for a cell 20 microns away from the focus, all the energy needed for lysis is delivered or impinges on the cell within about 25 nsec of initiation of the shockwave by the laser pulse. The cell explodes or is lysed in response in what is believed to be a few microseconds, i.e. in the range of 1–10 microseconds. The interaction of the shock wave with the cell rapidly disrupts the cell membrane thereby quickly releasing the cellular contents. Although the physics of the formation of the plasma and its cavitation bubble is not clearly understood, it is believed that there is a electron avalanche unique to generation of the localized plasma which produces the cavitation bubble. The illustrated embodiment also includes other mechanical stresses and optically induced damage that are generated by focused laser beams, which may not be associated with plasmas.

Figure 1A:
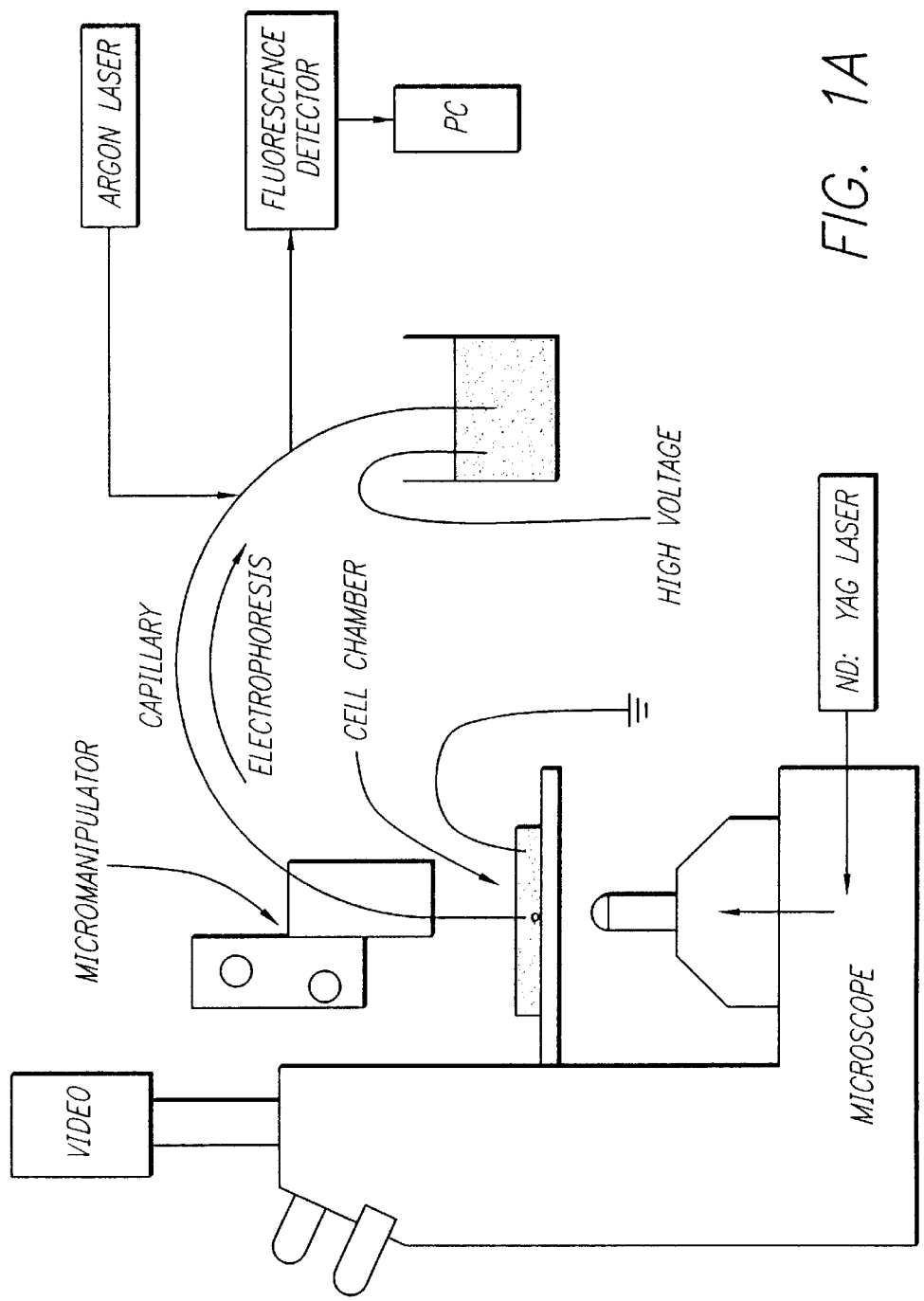
FIG. 1A is a schematic diagram of a system used for fast controllable cell lysis according to the invention.

FIG. 1A is a block diagram of the illustrated embodiment of a system in which fast controlled cell lysis is performed in combination with analysis by capillary electrophoresis. It must be understood that many components now known or later devised may be substituted into the system of FIG. 1A to perform equivalent functions. For example, although the illustrated embodiment contemplates laser induced fluorescence detection of analytes in an electrophoretic column, any measurement device or detection mechanism capable of analyte detection or analysis may be used.

The system, generally denoted by reference numeral 10, is comprised of a microscope 12 having a video ocular readout 14 displayed on a CRT screen 16 or recorded in a videotape recorder or digital recorder (not shown). In particular, as will be described below digital storage of the images and pattern processing in a computer system for automated cell processing and analysis is specifically contemplated as being within the scope of the invention. The CCD video camera system 14, 16 recorded the real time bright field image of cell 46 every 33 milliseconds. Lysis was determined from the appearance of the cell after the laser pulse. In most cases, the cell membrane was totally disrupted, leaving behind only a remnant of the membrane attached to cover slip 36 with the cellular contents suspended in the immediate vicinity of the cell as depicted in FIG. 2C. In the illustrated embodiment, electrophoresis was operator-initiated upon visualization of cell lysis, which was estimated to be a 300 msec response time. It is to be expressly understood that computer-controlled pattern recognition could be substituted for even faster reaction times or electrophoresis could be triggered directly off the laser pulse.

A pulsed Nd:YAG laser 18 is directed to microscope objective optics 20 of microscope 12. The laser system used for the cell lysing experiment included a frequency doubled Q-switched Nd:YAG laser such as manufactured as the Surelite I, by Continuum of Santa Clara, Calif. The laser was used to generate a single laser pulse of 10 to 100 $\mu$J with a 5 nsec pulse with a 532 nm wave length. The laser beam from laser 18 was directed into microscope 12, namely Axiovert 135 manufactured by Zeiss of Thornwood, N.Y. The laser pulse was focused to approximately 0.3 to 0.4 microns at its waist 50 as shown in FIG. 1B using microscope objective 20 (63 x, 1.25 n.a. Zeiss) at the interface of the cell chamber cover slip 36 and buffer solution 54. Cell 46 which was to be lysed was positioned 20/30 microns laterally to focal point 50 of the laser pulse. It is to be expressly understood, however, that in another embodiment direct interaction would be arranged, such as where the laser parameters were adjusted only to open a hole in the cell membrane to expel the cytoplasmic contents, leaving the nuclear material within. It must be understood that other types of lasers other than the one illustrated here may also be used to generate the shock wave. In addition to lysis of the cell, the nucleus of the cell which has been isolated or removed from the cell may by manipulated to recover the DNA or other nuclear material.

A fused silica capillary column 22 is positioned by means of a micromanipulator 24 which positions proximate inlet 26 of capillary 22 above a cover slip or slide 28 positioned on microscope stage 30. The buffer solution around the cell and above the cover slip is electrically grounded. The distal end 32 of capillary 22 is disposed in an electrolyte or buffer bath 34 in order to create a gravity siphon pressure through capillary 22 at proximate end 26. A high voltage power supply, model CZE 1000R manufactured by Spellman of Plainview, N.Y., was used to drive the electrophoresis in column or capillary 22. Fused silica capillary 22 had a 50 micron inner diameter and 360 micron outer diameter. The lumen walls were coated with a proprietary neutral coating manufactured by Supelco of Phoenix, Ariz. The coating was used to minimize the electroosmotic flow and thus shorten the migration times for the negatively charged, fluorophores used in these experiments. The total length of the capillary was 90 to 100 cm. The detection window was about 75 cm from inlet 48. Electrophoresis was performed in a biologically compatible buffer. The cell chamber served as an inlet reservoir and was held at ground potential. The outlet reservoir was held at 15 to 18 kV. Distal outlet 32 of capillary 22 was placed 5 centimeters below inlet 48. Inlet 48 of capillary 22 was used as a micropipette for introducing the cellular contents into capillary 22 after cell lysis.

After removing 5 mm of polyimide coating from capillary 22 above inlet 48, inlet 48 was mounted perpendicularly to cover slip 36 on micromanipulator 24. Micromanipulator 24 enabled precise positioning of capillary lumen 52 with respect to cell 46 to be lysed and loaded into capillary 22. Capillary 22 was washed with fresh buffer A for one to two minutes after every run. Gravitational siphon fluid flow was used to load capillary 22 with a fluorescein/Oregon Green free acid standard. The loaded volumes were calculated from Poiseulle's equation.

Capillary 22 includes an inspection window 38 upon which an excitation beam from Argon laser 40 is exposed. Optical window 38 in the polyimide coating of capillary 22 was created 75 to 85 cm from inlet 48. Capillary lumen 52 was interrogated by a focused laser beam from Argon ion laser 40. Fluorescence data were collected at a right angle to capillary 22 and to the laser beam from laser 40 with a microscope objective of 40× with a 0.75 n.a. Plan Fluor manufactured by Nikon of Melville, N.Y. The light was measured with a photomultiplier tube, a PMT R928 made by Hamamatsu, of Bridgewater, N.J. after spectral filtering with a 488 notch filter manufactured by Kaiser Optical Systems of Ann Arbor, Mich. and filtering with a band pass filter 535 DF55 made by Omega Optical of Brattleboro, Vt. The photomultiplier current was amplified and converted to a voltage with a preamplifier then digitized by a data acquisition board in a personal computer 44. The data were plotted and peak areas calculated using Origin written by Microcal of North Hampton, Mass. Induced fluorescence is detected by fluorescence detector 42 to create the electropherograms of FIGS. 4A–D through the use of a personal computer 44. Bath 34 is electrically coupled to high voltage source 36 to provide the electrophoretic force to cause analyte separation in capillary 22.

FIG. 1B is a highly enlarged side view of proximate end 26 of capillary 22 showing a single cell 46 disposed on cover slip 36 and positioned adjacent inlet 48 of proximate end 26 of capillary 22. Laser 18 is focused in a focal area, diagrammatically depicted as focal area 50 either in cover slip 36 or just below the fluid-to-cover slip interface on its upper surface. FIG. 1C is a bottom view of the enlarged depiction of FIG. 1B showing the planar relationship of the same elements and in particular the spatial overlap of cell 46 to inlet 48 and the proximity of laser focus 50.

By positioning inlet 48 of capillary 22 directly above cell 46 prior to lysis, as shown in FIG. 1C the cellular contents of the lysed cell are loaded into lumen 52 of capillary 22 by combination of the gravity siphon and electrophoresis at lysis. The force of the shock wave also conveys momentum to the cell fragments which drive them into the lumen of the capillary. As will be shown below the time required between the instant of the beginning of lysis and the loading within lumen 52 is significantly less than 33 msec. The absence of any manipulation of cell 46 prior to lysis and the extreme rapidity of the lysis itself results in minimal physiological effects on cell 46 up to the time of sampling. Once cell 46 is lysed, cellular reactions are terminated by diffusion, turbulent mixing or electrophoretic separation of reactants thus making more accurate snapshots of the intracellular composition possible. The technique in the illustrated embodiment is described in connection with adherent cells, but it is also applicable to nonadherent cells, which are either loaded physically into inlet 48 or held by laser microbeam optical tweezers (not shown). The improved rapidity of this technique, the absence of cell trauma prior to lysis and its application to both adherent and nonadherent single cells will expand the role of microanalytical single cell measurements. The applications of the present invention will be described in greater detail below.

Consider now a specific illustrated embodiment starting with the reagents used. Fluorescein diacetate (mixed isomers), fluorescein (fluorescein free acid), Oregon Green 488 carboxylic acid diacetate 6-isomer (Oregon Green diacetate), and Oregon Green 488 carboxylic acid 6-isomer (Oregon Green free acid), was prepared by and obtained from Molecular Probes of Eugene, Oreg. A buffer solution, which will be referenced here as buffer A is a physiologic extracellular buffer used as the electrolyte medium in capillary 22 between proximate end 26 and cover slip 36/ Buffer A is composed of 135 mM of NaCl, 5 mM of KCl, 10 mM of Hepes, 2 mM of $MgCl_2$, 2 mM of $CaCl_2$ and adjusted to a pH of 7.4 with NaOH from reagents purchased from Fisher Scientific of Pittsburgh, Pa.

Rat basophilic leukemia (RBL) cells, a tumor mast cell line, were used as the model system for the illustrated embodiment. The cells were grown at 37° C. and 5% $CO_2$ in Dulbecco's modified eagle medium (DMEM) supplemented with 10% fetal bovine serum and L-glutamine (584 mg/L). Penicillin (100 units per ml) and streptomycin (100 µg/ml), were added to the media to inhibit bacterial growth. Cell culture materials were obtained from Gibco BRL of Gaithersburg, Md. The cells were grown in a cell chamber and made by using Sylgard from Dow Corning of Midland, Mich., to attach a Teflon O ring of 15/16 inch outer diameter to a 25 mm diameter round number 1 glass cover slip. Cell attachment to the glass surface was enhanced by coating the cover slip with Cell-Tak made by Becton Dickinson of Bedford, Mass., prior to adding the cells to the cell chamber. Prior to use, the cells were allowed to grow in the supplemented medium for 12 to 24 hours after plating in the cell chamber. The cells were plated at concentrations determined empirically to produce approximately one cell in a 63× field of view at the time the laser exposure was made.

The cells were loaded with fluorescein diacetate and/or Oregon Green diacetate. These cell permeant compounds are not fluorescent until they are hydrolyzed by ubiquitous intracellular esterases after the compounds pass into the cell. Once the fluorescent free acid is formed, it is no longer cell permeant and remains trapped within the cell although the cells do transport the dye out over time via anionic transporters. For the single cell experiment cells grown in DMEM in a cell chamber were washed once in Buffer A. Solutions of fluorescein (20 nM) and/or Oregon Green (500 nM) diacetates were made in 400 µl buffer A plus 10 mM glucose immediately prior to use and added to the cell chamber after removing the wash buffer. The cells were incubated at room temperature in the dark for 30 minutes to load the fluorescent compounds into the cells. The cells were then washed five times in buffer A and used within 10 to 15 minutes thereafter. The amount of dye loaded into each cell by this method varies to some degree due to cell-to-cell differences in the hydrolysis of the diacetate and due to loss of the free acid from the intracellular space. Estimates of the moles of fluorescent marker obtained from each cell were made by comparison of fluorescent peak areas with comparison to standards in electropherograms Fresh buffer A, 10 ml per minute, was continually exchanged in the cell chamber during the course of the experiment in order to remove the dye expelled from the cells into the surrounding buffer. In the absence of the flow system, dye accumulated in the extracellular buffer over time, increasing the fluorescence baseline.

The temporal resolution of the biological measurements used for a single cell analysis is determined by the time between initiation of the sampling process and termination of cellular reactions involving the molecule(s) of interest. Termination of these reactions is achieved by separation of the reactants usually by mixing, diffusion and/or electrophoresis or by inactivation of the reactants, typically by denaturation of the proteins. Minimizing the time required for cell lysis and initiation of analysis, such as by capillary electrophoresis, enhances the temporal resolution of single cell biochemical analyses. As discussed below, cell lysis in msec time scales followed by loading of cellular contents into a capillary for separation detection dramatically improves the temporal resolution of capillary electrophoresis based chemical measurements of single cells.

Figure 2A:
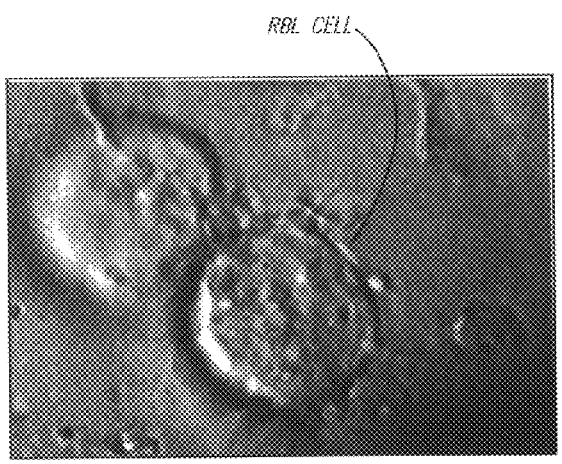
Figure 2B:
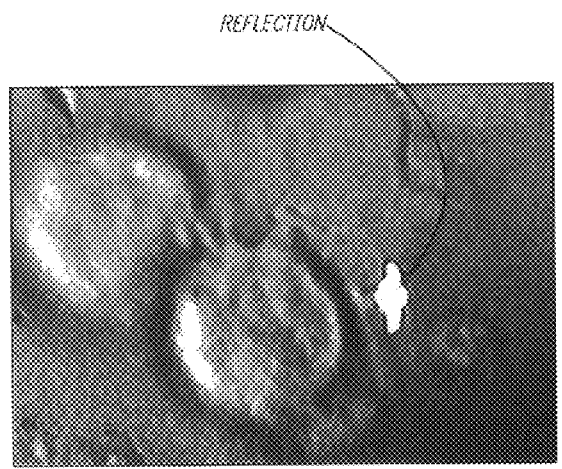

To determine the characteristics of a cell lysis by production of a shock wave, a single pulsed laser microbeam with an energy content in the range of 20–100 µJ was employed as described above to lyse the RBL cells while the video camera recorded the bright field image every 33 msec as depicted in the sequence of depictions in FIGS. 2A–B. FIG. 2A is a photodepiction of an RBL cell prior to lysis and FIG. 2B at the moment of lysis showing a reflection of the laser beam immediately to the right of a cell to be lysed. Thirty-three milliseconds thereafter as shown in FIG. 2C, the cell has been completely disrupted, leaving only fragments of the cell membrane. Substantially, all the cell contents are released within thirty-three msec subsequent to lysis and there is no substantial difference between the condition of the field of view at 2C and five seconds later as shown in FIG. 2D. Direct, localized attenuation of a portion of the plasma membrane is performed by focusing the laser pulse at lower energy densities directly on the cell membrane. In experiments described here, complete lysis is achieved without direct exposure of the cell to the laser beam. In this way, neither photodestruction nor photobleaching of intracellular species occurs. In the lysis of the cell the beam was positioned 20–30 microns to one side of cell 46, as depicted in FIG. 2B. The shock wave was generated by focusing the pulsed laser beam with a 0.3 to 0.5 micron diameter at its waist 50 within coverslip 36 just below the coverslip-to-buffer interface. The same shock wave effect could also be obtained by using other microscope objectives ranging in magnification form 40× to 100×.

RBL cells contain histamine and serotonin within secretory granules. These granules appear as small particles released upon cell lysis that move by Brownian motion. Using lower energies, 10–20 µJ, to generate the shock wave, the cell membrane appears to be permeabilized by the shock wave. These cells become spherical after the shock wave has passed through the cells and the cellular contents, namely the granules, leak out of the cell over 20–30 video frames. At higher energies above 20 µJ, the membrane is completely disrupted, leaving only remnants of the membrane present in the first video frame as shown in FIG. 2C after impingement of the shock wave. The actual time period over which lysis occurs is much shorter than 33 msec, and possibly as brief as 25–30 nsec. 33 msec is chosen here only as the lowest time resolution of the video analysis which was limited by the 30 frame per second video rate. At these higher energies the secretory granules are again seen in the immediate vicinity, that is within about 10 microns of the remnants of the plasma membrane. The fact that the secretory granules remain localized suggests that only limited dilution of cellular contents occurred at the time of lysis. By increasing the beam energy over the range of 20–100 µJ, cells could be lysed at greater distances from its focal point.

This laser-based method of cell lysis allows for local attenuation of a cell membrane in such a manner that the degree and field of cell lysis can be selectively controlled. This controllability makes it possible to obtain subcellular measurements of small cells by lysing a portion of the cell, i.e. lysis of a cell extension or rupture of the nucleus where the genetic material resides.

Figure 3A:
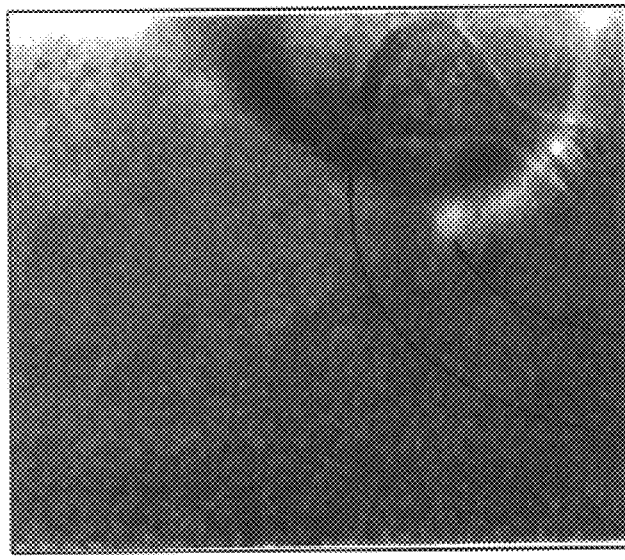
FIGS. 3A–C are a series of video still frame images taken every 33 msec of a single cell positioned at the inlet of a capillary.
Figure 3B:
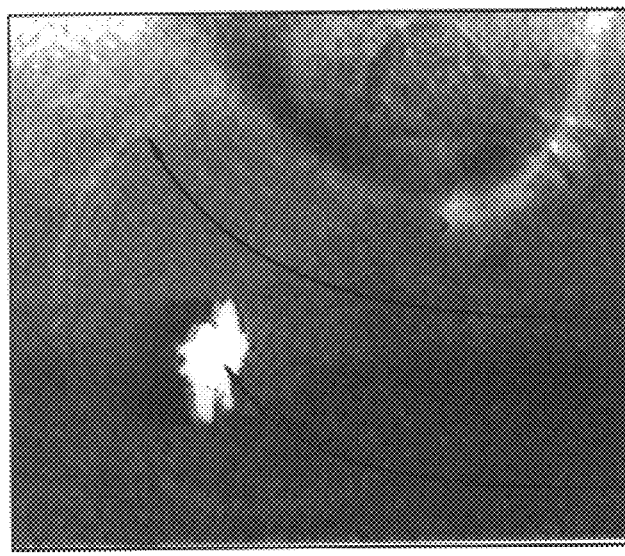

In each case of cell lysis, a small divot appears in glass coverslip 36 at the point where the laser beam was focused. In some instances, a bubble with a diameter of less than 5–10 microns appeared in the first frame following the laser pulse at the intersection of the laser beam and the glass buffer interface. The bubble was absent in subsequent frames. In other experiments, the circular wave could be seen emanating from the location of the laser beam in a video frame coincident with the pulse. Thirty-three milliseconds later the cell was obliterated, and the wave had disappeared as depicted in the series of frame shots shown in FIGS. 3A, 3B and 3C. The divot, bubble and wave further support the contention that a plasma is formed on cover slip 36 thereby producing cavitation and a shock wave.

Figure 3C:
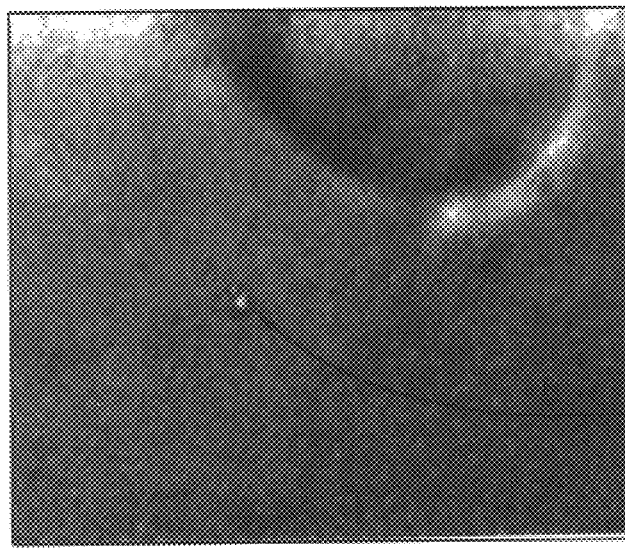

To demonstrate that the contents of an adherent RBL cell are then loaded into capillary 22 after lysis, a single RBL cell 46 containing fluorescein was positioned below in proximate inlet 48 of lumen 52 of capillary 22. Inlet 48 of capillary 22 was approximately 15–25 microns above cell 46, although capillary 22 could be positioned flush with cover slip 36 so the cell actually sat within the entrance to lumen 52 if desired. Cell 46 was lysed as described above and electrophoresis was initiated upon cell lysis. Analysis of the video images show the cellular contents had disappeared within 33 msec after the lysis pulse as shown in FIG. 3C. The cellular contents had thus been loaded within capillary 22 in less than 33 msec. In some experiments the plasma membrane remnants remain attached to glass-coverslip 36 while in other experiments the remnants were also loaded into capillary 22. The current and migration times of fluorophores from the cells were the same in both cases. In these experiments, the cellular contents were loaded into capillary 22 by gravity siphon flow with some later contribution from electrophoresis. Although not utilized in these experiments, by triggering the capillary electrophoretic power supply with the trigger pulse of the laser, electrophoresis could be initiated coincidentally with the lysis pulse. The use of a capillary with charged lumenal walls allows the use of electroosmotic flow, and loading the cell's contents by the gravity siphon flow could be eliminated, if desired. Some loading also occurs by virtue of the laser induced shockwave.

Figure 4:
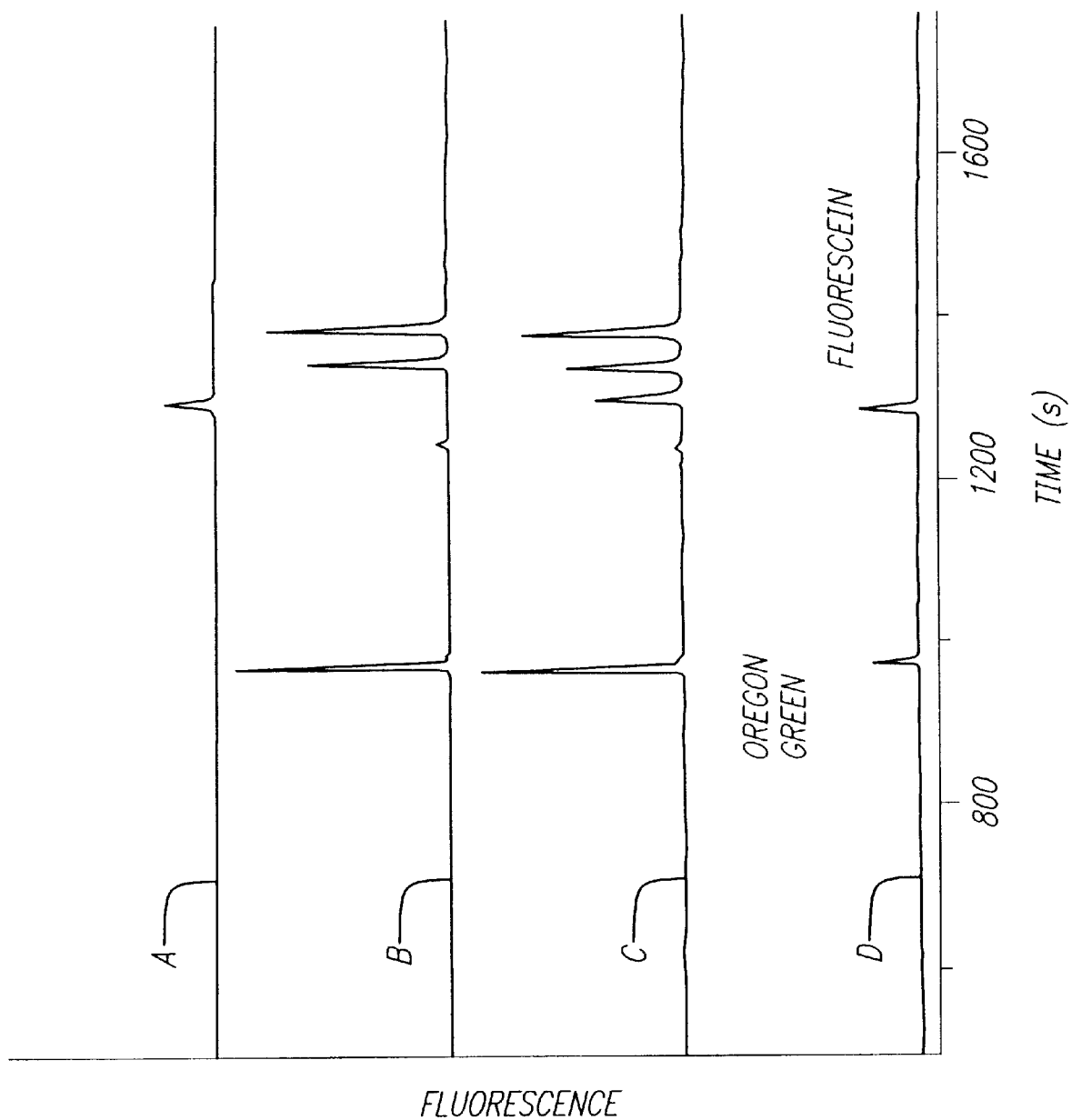
FIG. 4 shows four stacked electropherograms of single cells and a free acid standard containing the fluorophores, fluorescein, and/or Oregon Green.

Turn now and consider the electrophoretic traces shown in FIG. 4. All electrophoretic runs were performed on the same day using the same capillary, namely a 100 cm capillary having a 50 micron inner diameter, a 360 micron outer diameter, a detection window 85 cm from the inlet with an applied voltage of 15 kV at 60 microamp. The amount of fluorophores was determined by comparison with standards. Trace A of FIG. 4 shows the detection of fluorescein which was loaded into the cell and which was detected after cell lysis and electrophoresis was performed. A single peak containing fluorescein is depicted. Trace B of FIG. 4 is an electrophoretic trace from a single cell loaded with Oregon Green. The four reproducible peaks of Oregon Green diacetate are clearly illustrated. The fluorophore in the largest peak corresponds to free acid. Trace C of FIG. 4 is the trace from a single cell loaded with both fluorescein and Oregon Green showing the superposition of traces A and B. Trace D of FIG. 4 shows the detection of Oregon Green and fluorescein in the free acid standards.

Trace A of FIG. 4 shows a single peak with the same migration time as that of fluorescein in the buffer in the electropherogram of trace D, thereby confirming that the cell's contents were in fact loaded into capillary 22. Electrophoretic traces (not shown) of cells not containing a fluorescent marker showed no peaks. Likewise, when inlet 48 of capillary 22 was placed at a distance just beyond the field of view from a fluorescein containing cell, the fluorescent baseline of the electropherogram (not shown) remained flat after cell lysis, indicating failure to load the cell contents within capillary 22.

In some experiments more than one cell was present in the vicinity of inlet 48. By employing higher laser energies to lyse the cell immediately below inlet 48, multiple cells could be lysed. Peaks corresponding to these adjacent cells could then be seen separately in the electropherogram. It is anticipated, therefore, that in most applications cell lysis will be controlled or the density of the cell population maintained so that only a single cell's contents are loaded. However, this is not to necessarily exclude applications where lysis of multiple cells by the same laser pulse might for some reason be desired.

A series of experiments were conducted in which RBL cells were loaded with fluorescein or Oregon Green alone or in combination. A single cell containing the fluorophore was then lysed and its contents loaded into capillary 22 and electrophoresis performed as described above. Traces A–C of FIG. 4 show representative traces for these experiments. Interestingly, while electrophoresis traces of cells loaded with fluorescein diacetate alone demonstrated a single peak, cells with Oregon Green diacetate alone consistently demonstrated three distinct peaks of nearly equal magnitude and a smaller fourth peak. Migration time of the initial Oregon Green peak was identical to that Oregon Green free acid in buffer. The subsequent peaks were not seen in the electrophoretic traces of the Oregon Green free acid standard. No fluorescent peaks were identified when Oregon Green diacetate ($3.8 \times 10^{-15}$ mol) was electrophoresced in buffer. The two additional major peaks in the Oregon Green traces may be forms of partially hydrolyzed Oregon Green diacetate or the additional peaks may be impurities that are concentrated within the cell. As a result of the occurrence of these additional peaks in the Oregon Green signal, it is possible to demonstrate the resolution of five distinct species from a single cell as shown in trace C of FIG. 4.

Figure 5:
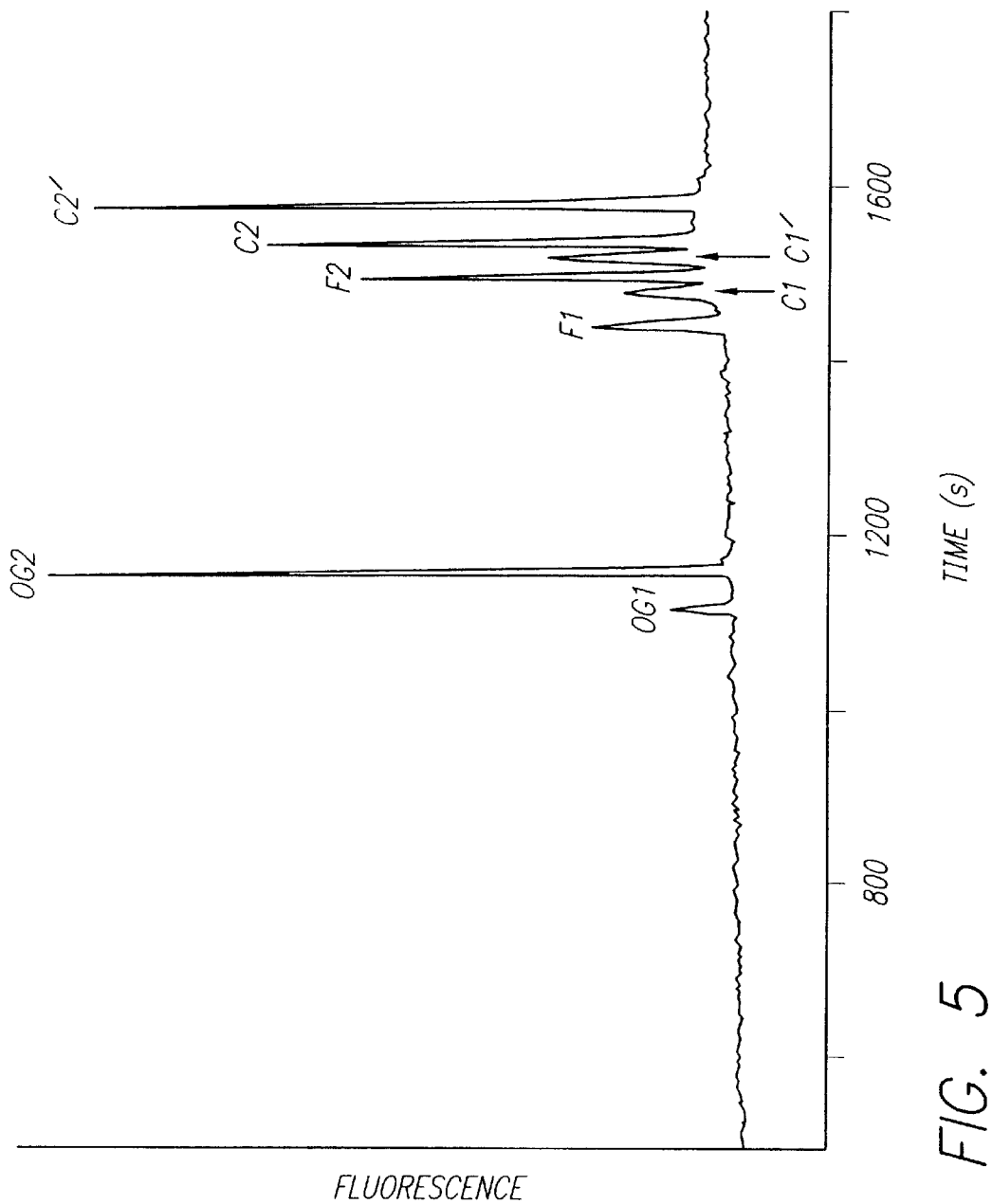
FIG. 5 is an electropherogram of two cells loaded with both fluorescein and Oregon Green, which cells were lysed in sequence and then loaded in sequence into the capillary. The subscript "1" indicates the peaks from the cell lysed first and the subscript "2" indicates the peaks from the cell lysed second in time.

As the demonstration of feasibility of serial analysis of the contents of two cells using the technique of the invention, capillary 22 was loaded with two cells lysed in succession. Two cells were contained in the same cell chamber and loaded with fluorescein and Oregon Green diacetates in a similar manner. A single loaded cell below a proximate inlet 48 of capillary 22 was lysed and its contents introduced into capillary 22 by gravity siphon flow. The second cell was then centered below inlet 48 during which time buffer continued to flow into the capillary by gravity. The second cell was lysed and electrophoresis was performed immediately following lysis. Thus, the contents of the second cell were loaded by a combination of gravity, electrophoresis and possibly momentum created by the laser induced shock wave. The electropherogram of FIG. 5 shows the analytes from each cell as distinct peaks. Fluorescent signals from the first cell denoted by subscript "1" are lower than those for the second cell denoted by subscript "2". This difference in signal intensity is most likely due to the biologic diversity of cellular uptake and differences in the metabolism of the two cells.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

Although there is no intended limit to the applications to which the invention can be applied, it is expressly contemplated that such modifications within the skill of the art as may be needed to use the invention in diagnostic biopsies including DNA analysis using polymerase chain reactions or other biochemical methods in both human and animal medicine are included within the scope of the claims. The use of the invention in combination with conventional pathology techniques to provide confirmation or automation of pathological identification of diseased states is included. Significant application of the invention in the selection and analysis of hybridoma cells is specifically intended. The technique has clear application to drug efficacy testing both in vitro and in vivo and to gene sequencing and therapy. As mapping the human genome proceeds, the invention will be a useful tool in detecting and diagnosing variances in gene expression, RNA, and protein function and in correcting or mitigating these deficiencies. The invention is broadly applicable to other species and genomes as well.

The use of any type of mechanism beyond siphon, electrophoretic, electroosmotic and shock wave forces to collect the cell contents into a pipette is expressly included in the scope of the invention. Analysis by polymerase chain reactions or any other microanalytical techniques now known or later devised is considered as equally applicable as the described electrophoretic laser induced fluorescence. The controllability of cell selection will allow new applications where analysis of a cell marked by chemical or other techniques is performed. Whereas the illustrated embodiment describes a fluid buffer in which the cell is cultured, lysed and its contents then extracted in a flow, it is expressly contemplated that the techniques can be modified from those illustrated to include any type of medium including solid or semisolid matrices or tissues into which collection and fiber optics can be inserted. For example biologic matrices mounted on silicon or solid substrates can be combined with the claimed technique to provide partial or completely lysed cell analysis in combination with electrochemical measurement of the cells and cell contents and of tissue sections. The analysis of both endogenous cellular components such as DNA, RNA, proteins, small organic molecules such as second messengers and others as well as exogenous or artificial components introduced into the cell, such as enzyme substrates, molecules with bromodeoxyuridine or other chemical markers that can be used to identify other molecules, are specifically anticipated..

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for lysing and collecting the contents of one or more selected cells or one or more cellular components thereof, comprising:

controllably selecting at least one of a plurality of cells or cellular components thereof in a medium;

positioning a selected cell, cells or cellular component thereof in proximity to a microcollection device;

producing a laser generated shock wave in close proximity to said selected cell, cells or cellular component thereof in said medium such that said cell, cells or cellular component thereof is lysed to permit at least a portion of said contents of said selected cell, cells or cellular component thereof to be accessible to said medium without substantial alteration; and collecting said accessible contents of said cell, cells or cellular component by means of said microcollection device.

2. The method of claim 1 wherein controllably selecting at least one of a plurality of cells or cellular components thereof comprises identifying and relatively positioning said selected cell, cells, or cellular component thereof.

3. The method of claim 2 where relatively positioning said selected cell, cells or cellular component thereof in said medium comprises adhering said cell, cells or cellular component thereof to a substrate disposed at least adjacent to said medium.

4. The method of claim 2 where said cell, cells or cellular component is free floating and where relatively positioning said selected cell, cells or cellular component thereof in said medium comprises temporarily holding said cell, cells or cellular component thereof in a position in said medium by laser microbeam optical tweezers.

5. The method of claim 2 where said cell, cells or cellular component is free floating and where relatively positioning said selected cell, cells or cellular component thereof in said medium comprises temporarily holding said cell, cells or cellular component thereof in a position in said medium by adhesion of a mechanical micromanipulator-held pipette or other device to said cell, cells or cellular component thereof.

6. The method of claim 2 where said cell, cells or cellular component is free floating and where relatively positioning said selected cell, cells or cellular component thereof in said medium comprises positioning said cell, cells or cellular component thereof in a confined enclosure.

7. The method of claim 6 where said cell, cells or cellular component is free floating and where positioning said cell, cells or cellular component thereof in said confined enclosure comprises positioning said cell, cells or cellular component thereof in an inlet to an analysis device.

8. The method of claim 1 wherein collecting at least a portion of said accessible contents of said cell, cells, or cellular component thereof comprises stopping reactions of biochemical reactants obtained from said lysed selected cell, cells, or cellular component thereof to permit subsequent analysis of said biochemical reactants in the state which existed approximately at the time of lysing.

9. The method of claim 1 where collecting at least a portion of said contents of said lysed cell, cells or cellular component thereof collects said cell, cells or cellular component thereof in an electrophoretic column or channel.

10. The method of claim 1 where producing a laser generated shock wave comprises focusing a pulsed laser beam at a position proximate to said cell, cells, or cellular component thereof, without focusing on said cell, cells, or cellular component thereof, and generating said shock wave.

11. The method of claim 1 where producing a laser generated shock wave comprises focusing a pulsed laser beam directly in or on said cell, cells or cellular component thereof and generating said shock wave.

12. The method of claim 11 where focusing a pulsed laser beam directly in or on said cell, cells or cellular component to lyse said cell, of cells or cellular component defines an opening in said cell, cells or cellular component to lyse only cytoplasmic contents therefrom.

13. The method of claim 1 where collecting at least a portion of said contents of said lysed cell, cells or cellular component thereof is by means of fluid flow of said medium.

14. The method of claim 13 where collecting at least a portion of said contents of said lysed cell, cells or cellular component thereof is by means of siphon fluid flow of said medium.

15. The method of claim 13 where collecting at least a portion of said contents of said lysed cell, cells or cellular component thereof is by means of force from said shock wave imparted to said contents.

16. The method of claim 13 where collecting at least a portion of said contents of said lysed cell, cells or cellular component thereof is by means of electroosmotic fluid flow.

17. The method of claim 1 where collecting at least a portion of said contents of said lysed cell, cells or cellular component thereof is by means of electrophoresis through said medium.

18. The method of claim 1 further comprising analyzing said collected cell, cells or cellular component contents in an analysis device.

19. The method of claim 18 where collecting at least a portion of said contents of said lysed cell, cells or cellular component thereof in said analysis device collects said cell, cells or cellular component thereof in an electrophoretic column or channel.

20. The method of claim 18 where analyzing said collected cell or cellular component contents is by means of laser induced fluorescence.

21. The method of claim 1 further comprising utilizing said collected cell, cells or cellular component contents.

22. The method of claim 1 where collecting said accessible cell or cellular component contents by means of said microcollection device comprises collecting said accessible cell or cellular, component contents in a capillary of a micropipette.

23. The method of claim 1 where collecting said accessible cell or cellular component contents by means of said microcollection device comprises collecting said accessible cell or cellular component contents in a microfabricated channel.

24. The method of claim 1 where collecting said accessible cell or cellular component contents by means of said microcollection device comprises aspirating said accessible cell or cellular component contents into said microcollection device.

25. The method of claim 24 where aspirating said accessible cell or cellular component contents into said microcollection device comprises aspirating said accessible cell or cellular component contents into a microlumen of a capillary of a micropipette.

26. The method of claim 24 where aspirating said accessible cell or cellular component contents into said microcollection device comprises aspirating said accessible cell or cellular component contents into a microfabricated channel.

27. The method of claim 1 where collecting said accessible cell or cellular component contents by means of said microcollection device comprises collecting said accessible cell or cellular component contents within one second of producing a laser generated shock wave to lyse said cell, cells or cellular component.

28. The method of claim 1 where collecting said accessible cell or cellular component contents by means of said microcollection device comprises collecting said accessible cell or cellular component contents within 33 msec of producing a laser generated shock wave to lyse said cell, cells or cellular component.

29. The method of claim 1 where collecting said accessible cell or cellular component contents by means of said microcollection device comprises collecting said accessible cell or cellular component contents within 10 microseconds of producing a laser generated shock wave to lyse said cell, cells or cellular component.

30. The method of claim 1 where collecting said accessible cell or cellular component contents by means of said microcollection device comprises collecting said accessible cell or cellular component contents within 1 microsecond of producing a laser generated shock wave to lyse said cell, cells or cellular component.

31. An apparatus for lysing and collecting the contents of one of a plurality of cells or cellular components thereof in a medium comprising;
   a cell selector to controllably select at least one of said cells or cellular components thereof;
   a laser for generating a shock wave pulse to lyse said at least one selected cell or cellular component at a location in said medium in sufficiently close proximity to said selected cell or cellular component such that said cell or cellular component is lysed to permit at least a portion of the contents of said selected cell or cellular component to be accessible to said medium; and
   a microcollection device to capture at least a portion of said contents of said lysed cell or cellular component thereof in a form having no substantial difference between the condition of said contents before and after lysis.

32. The apparatus of claim 31 further comprising an analysis device for analyzing said contents in a form having no substantial difference between the condition of said contents before and after lysis.

33. The apparatus of claim 32 wherein said microcollection device delivers at least said portion of said contents of said lysed cell or cellular component to said analysis device within one second of lysis of said cell or cellular component.

34. The apparatus of claim 32 wherein said microcollection device delivers at least said portion of said contents of said lysed cell or cellular component to said analysis device within 33 msec of lysis of said cell or cellular component.

35. The apparatus of claim 32 wherein said microcollection device delivers at least said portion of said contents of said lysed cell or cellular component to said analysis device within 1–10 microseconds of lysis of said cell or cellular component.

36. The apparatus of claim 32 wherein said analysis device comprises a means for performing polymerase chain reactions on said contents, a means of separating products of said polymerase chain reactions, and a means for detecting separated molecules.

37. The apparatus of claim 32 wherein said microcollection device delivers said portion of said contents of said lysed cell or cellular component to said analysis device by flowing said medium past said cell or cellular component during lysis.

38. The apparatus of claim 32 wherein said microcollection device delivers said portion of said contents of said lysed cell or cellular component to said analysis device by providing electrophoresis in said medium between said analysis device and said cell or cellular component during lysis thereof.

39. The apparatus of claim 32 wherein said microcollection device delivers said portion of said contents of said lysed cell or cellular component to said analysis device by providing an electroosmotic flow in said medium between said analysis device and said cell or cellular component during lysis thereof.

40. The apparatus of claim 32 wherein said microcollection device delivers said portion of said contents of said lysed cell or cellular component to said analysis device by providing force from a shock wave in said medium to move said cell or cellular component into said analysis device during lysis of said cell or cellular component.

41. A method for fast lysing and collecting the contents of one of a plurality of cells, group of cells or cellular components thereof in a medium comprising:

controllably selecting at least one of said plurality of cells, group of cells or cellular components thereof by relative placement of said selected cell, group of cells or cellular component proximate to a channel or lumen;

lysing said selected cell, group of cells or cellular component thereof with a laser generated shock wave pulse sufficiently in close proximity to said selected cell, group of cells or cellular component in said medium to permit at least a portion of the contents of said selected cell, group of cells or cellular component to be accessible to said medium;

collecting at least a portion of said contents of said lysed cell, group of cells, or cellular component thereof in a substantially unaltered form in said channel or lumen within one second of lysis for subsequent analysis; and stopping further substantial biologic reactions in said contents after lysis.

42. The method of claim 41 wherein said laser generated shock wave in close proximity to said selected cell, group of cells or cellular component.

43. The method of claim 41 further comprising simultaneously mixing said contents of said lysed cell, group of cells or cellular component thereof when collecting at least a portion of said contents of said lysed cell, group of cells or cellular component thereof.

44. The method of claim 41 wherein said portion of said contents of said cell, group of cells or cellular component thereof is collected within 33 msec or less of lysis of said cell, group of cells or cellular component.

45. The method of claim 41 wherein said portion of said contents of said cell, group of cells or cellular component thereof is collected within 1–10 microseconds of lysis of said cell, group of cells or cellular component.

* * * * *

UNITED STATES PATENT AND TRADEMARK OFFICE
CERTIFICATE OF CORRECTION

PATENT NO. : 6,156,576
DATED : December 5, 2000
INVENTOR(S) : Allbritton

Page 1 of 1

It is certified that error appears in the above-identified patent and that said Letters Patent is hereby corrected as shown below:

To be added in the Second Paragraph of the Specification:

"This invention was made with Government support under Grant Nos. DE-FG03-91ER 61227, awarded by the Department of Energy, RR01192, RR06961 both awarded by National Institutes of Health and N00014-94-0874 awarded by the Office of Naval Research. The Government has certain rights in this invention."

Signed and Sealed this

Twenty-eighth Day of August, 2001

Attest:

*Nicholas P. Godici*

NICHOLAS P. GODICI
*Attesting Officer*   *Acting Director of the United States Patent and Trademark Office*